United States Patent [19]

Baumann et al.

[11] 4,161,589
[45] Jul. 17, 1979

[54] SPIRODIPYRANS

[75] Inventors: Hans Baumann, Wachenheim; Andreas Oberlinner, Ludwigshafen, both of Fed. Rep. of Germany

[73] Assignee: BASF Aktiengesellschaft, Ludwigshafen, Fed. Rep. of Germany

[21] Appl. No.: 932,015

[22] Filed: Aug. 8, 1978

[30] Foreign Application Priority Data

Aug. 18, 1977 [DE] Fed. Rep. of Germany ....... 2737207

[51] Int. Cl.² .......................................... C07D 493/10
[52] U.S. Cl. ..................................... 544/70; 544/58; 544/60; 544/61; 544/150; 544/230; 544/378; 260/326.1; 428/411
[58] Field of Search .................. 544/70, 58, 60, 61, 544/230, 150, 378; 260/326.1, 326.11 S

[56] References Cited

FOREIGN PATENT DOCUMENTS 2363702 10/1975 Fed. Rep. of Germany ...... 260/326.11

*Primary Examiner*—Natalie Trousof
*Assistant Examiner*—R. W. Ramsuer
*Attorney, Agent, or Firm*—Oblon, Fisher, Spivak, McClelland & Maier

[57] ABSTRACT

Spirodipyrans of the formula

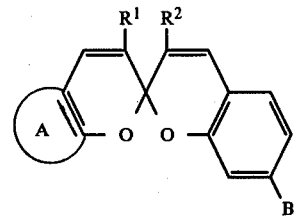

where
A is the radical of a fused benzene ring or 2,1-naphthalene ring, the rings being unsubstituted or substituted by alkyl, alkoxy, nitro, chlorine, bromine or carbalkoxy,
$R^1$ is alkyl, phenyl, substituted alkyl or phenalkyl and
$R^2$ is hydrogen, or
$R^1$ and $R^2$ together are trimethylene which is unsubstituted or substituted by 1, 2 or 3 alkyl and
B is N-morpholinyl, substituted morpholinyl, thiomorpholinyl-S-dioxide, N-(N'-alkyl)-piperazinyl or N-isoindolinyl, and pressure-sensitive recording materials containing these spirodipyrans as dye-forming components.

With electron acceptors, the spirodipyrans give reddish violet to blue colorations, while no coloration is produced on paper which has not been coated with an electron acceptor.

7 Claims, No Drawings

SPIRODIPYRANS

The present invention relates to spirodipyrans of the general formula

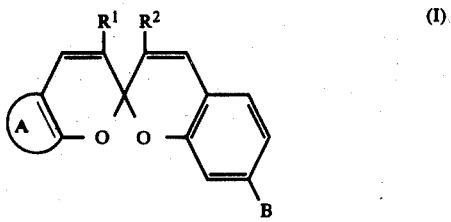

where

A is the radical of a fused benzene ring which is unsubstituted or is substituted by alkyl of 1 to 4 carbon atoms, alkoxy of 1 to 4 carbon atoms, nitro, chlorine, bromine or carboalkoxy (where alkoxy is of 1 to 6 carbon atoms), or is the radical of a naphthalene ring fused in the 2,1-position, which is unsubstituted or substituted by chlorine, bromine or carboalkoxy (where alkoxy is of 1 to 6 carbon atoms), $R^1$ is alkyl of 1 to 16 carbon atoms or is phenyl which is unsubstituted or substituted by alkyl of 1 to 4 carbon atoms, alkoxy of 1 to 4 carbon atoms, chlorine or bromine, or is phenalkyl of 7 to 10 carbon atoms and $R^2$ is hydrogen, or $R^1$ and $R^2$ together are a trimethylene bridge which is unsubstituted or in which one, two or three H atoms are replaced by alkyl of 1 to 12 carbon atoms, and B is N-morpholinyl, which is unsubstituted or substituted by one or two methyl, or is N-thiomorpholinyl-S-dioxide, N-(N'-alkyl)-piperazinyl (where alkyl is of 1 to 4 carbon atoms) or N-isoindolinyl.

The spirodipyrans of the formula I are pale-colored or colorless compounds, the solutions of which, in an inert organic solvent, give colorations, ranging from reddish violet to blue, on contact with an electron acceptor. Typical examples of electron acceptors are carboxylic acids, mineral acids, kaolin, bentonite, activated clay, aluminum silicate, attapulgite or any other clay, acidic polymeric materials, e.g., condensation products of phenols and/or phenolsulfonic acids, and metal oxides and salts, e.g., zinc oxide, aluminum oxide, zinc chloride, iron stearate and cobalt naphthenate.

Because of these properties, the novel spirodipyrans of the formula I can be used as dye-forming components for pressure-sensitive recording materials and copying materials.

When used in pressure-sensitive copying systems, the spirodipyrans according to the invention, of the formula I, have the advantage that the dye-forming component exhibits virtually no tendency to produce a coloration on uncoated coating base paper. Hence, on making a copy, a mirror image does not appear on the back of the sheet coated with the dye-forming component. For the same reason, in the event of unintentional destruction of the capsules, no staining of the side of the sheet which carries the microcapsule layer occurs.

Advantageously, the spirodipyrans of the invention are enclosed in microcapsules in the conventional manner, in the form of a solution or suspension in an organic solvent, e.g., a chloroparaffin, halogenated or partially hydrogenated biphenyl, alkylbenzene, alkylnaphthalene, alkylated dibenzylbenzene, paraffin or mineral oil, or a conventional solvent such as toluene or xylene, and the paper surface is coated with the microcapsules, using binders and other auxiliaries, e.g., spacer materials.

Pressure-sensitive papers are obtained which when used for writing or typing, in contact with electron acceptors, give an image ranging from reddish violet to blue.

Suitable processes for the manufacture of microcapsules are described, for example, in U.S. Pat. Nos. 2,800,457 and 2,800,458 and German Pat. No. 2,119,933.

Since the spirodipyrans (I) of the invention are more stable, even in aqueous suspension, than are dye-forming components containing dialkylamino groups, they give virtually colorless microcapsule dispersions.

It is also possible to disperse the spirodipyrans according to the invention, of the general formula I, in wax or oil-wax mixtures, using the process described in U.S. Pat. No. 3,103,404, and to use such mixtures to coat base materials, e.g., films or paper. Pressure-sensitive materials are obtained, which can be used for producing copies on papers coated with electron acceptors, and which, after use, are removed like carbon paper.

Specific examples of suitable substituents—in addition to those already mentioned—which may be present on the fused phenyl radical (A) are, amongst alkyl of 1 to 4 carbon atoms, isopropyl, n-propyl, isobutyl, sec.-butyl, tert.-butyl and especially methyl or ethyl; amongst alkoxy of 1 to 4 carbon atoms, isopropoxy, propoxy, n-butoxy, isobutoxy and preferably methoxy or ethoxy; amongst carboalkoxy (where alkoxy is of 1 to 6 carbon atoms), carbo-n-hexoxy and preferably carboalkoxy, where alkoxy is of 1 to 4 carbon atoms, e.g., carbomethoxy, carboethoxy, carbo-n- and -i-propoxy, carbo-butoxy, carbo-isobutoxy, carbo-tert.-butoxy and carbo-sec.-butoxy.

Suitable substituents present on the fused 2,1-naphthalene system (A) are, in addition to chlorine and bromine, the above carboalkoxy groups, where alkoxy is of 1 to 6 carbon atoms, and preferably those where alkoxy is of 1 to 4 carbon atoms.

Particularly preferred meanings of A are unsubstituted fused benzene radical or 2,1-naphthalene radical.

Where $R^1$ is alkyl of 1 to 16 carbon atoms, specific examples are methyl, ethyl, n-propyl, isopropyl, n-butyl, sec.-butyl, isobutyl, tert.-butyl, n-pentyl, isopentyl, n-hexyl, n-nonyl, i-nonyl, n-octyl, i-octyl, n-decyl, i-decyl, n-dodecyl, i-dodecyl and n-hexadecyl. Amongst these, alkyl of 1 to 4 carbon atoms are preferred.

$R^1$ may, as stated, be unsubstituted phenyl; if it is substituted phenyl, specific examples are alkoxyphenyl, where alkoxy is of 1 to 4 carbon atoms, e.g., butoxyphenyl, propoxyphenyl, methoxyphenyl and ethoxyphenyl, and alkylphenyl, where alkyl is of 1 to 4 carbon atoms, e.g., isobutylphenyl, tert.-butylphenyl, sec.-butylphenyl, propylphenyl, isopropylphenyl, ethylphenyl and methylphenyl, as well as chlorophenyl and bromophenyl.

Specific examples of phenalkyl radicals $R^1$ are benzyl, β-phenylethyl, β-phenylpropyl, γ-phenylpropyl, γ-phenylbutyl and δ-phenylbutyl.

Amongst the radicals mentioned as examples of $R^1$, alkyl of 1 to 4 carbon atoms, methoxyphenyl, ethoxyphenyl, ethylphenyl, methylphenyl and chlorophenyl are preferred, alkyl of 1 to 4 carbon atoms being very particularly preferred.

Specific examples of trimethylene groups formed by $R^1$ and $R^2$ together are trimethylene, $\alpha,\gamma,\gamma$-trimethyltrimethylene, $\beta$-tert.-butyltrimethylene, $\beta$-n-octyltrimethylene, $\beta$-n-dodecyltrimethylene and $\beta$-n-nonyltrimethylene.

Preferred meanings of B are N-isoindolinyl and especially N-morpholinyl.

For use as dye-forming components, spirodipyrans of the formula

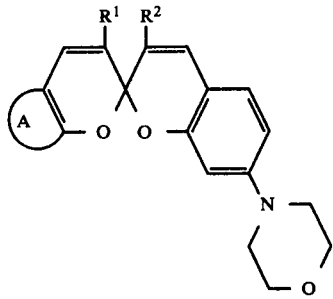
(Ia)

where $R^1$, $R^2$ and A have the above meanings, are preferred, for performance reasons.

For technical reasons, compounds of the formula Ia, where $R^2$ is hydrogen and $R^1$ is alkyl of 1 to 4 carbon atoms, are preferred. Amongst these, the compounds where $R^2$ is hydrogen, $R^1$ is alkyl of 1 to 4 carbon atoms and A is the unsubstituted radical of a fused benzene ring or 2,1-naphthalene ring are particularly preferred.

Very particularly preferred dye-forming components are

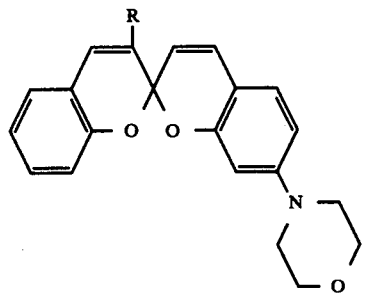
(Ib)

and

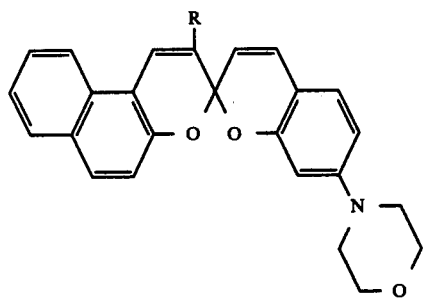
(Ic)

where R is —CH$_3$, —C$_2$H$_5$, —CH(CH$_3$)$_2$ or —CH$_2$—CH(CH$_3$)$_2$.

The dye-forming components are synthesized in the conventional manner, in accordance with the equation shown below, by cyclizing an o-hydroxyaryl-styryl compound of the formula IV. The latter is obtained, for example, by condensing a benzopyrylium salt of the formula II with a N-substituted p-aminosalicylaldehyde of the formula III. The compound of the formula IV can also be manufactured by reacting a chalcone of the formula V with an aldehyde of the formula III, in the conventional manner, in accordance with the equation also shown below.

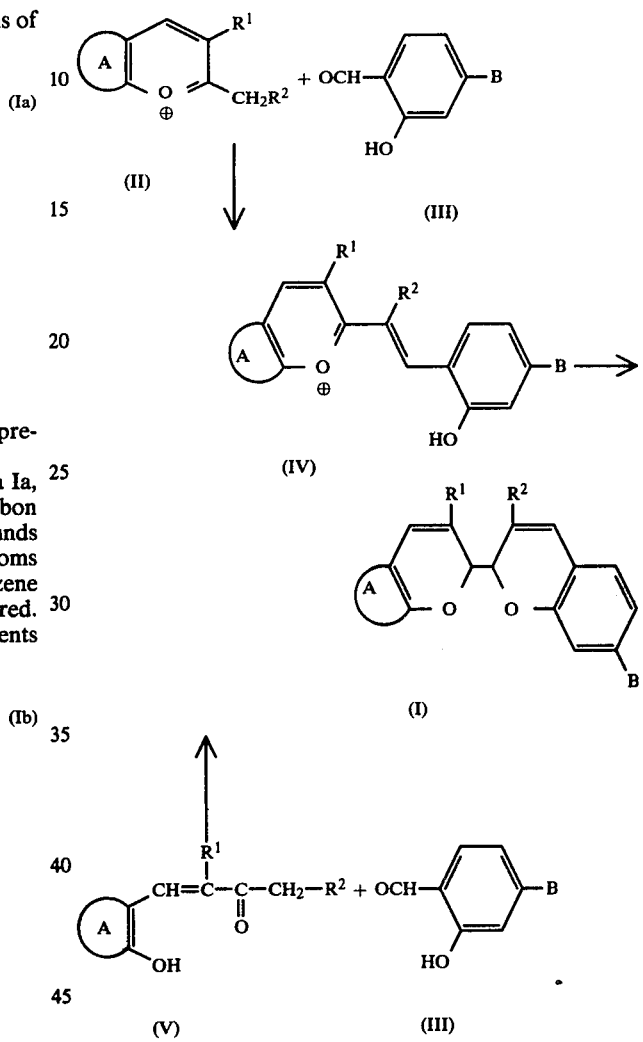

The condensation is advantageously carried out in an inert organic solvent, such as an alcohol, carboxylic acid, carboxylic acid anhydride, carboxylic acid amide or hydrocarbon, or in acetonitrile, in the presence or absence of an acid or basic condensing agent, e.g., zinc chloride, phosphoric acid, hydrogen chloride, toluenesulfonic acid, boric acid, pyridine, piperidine, triethylamine or ammonium acetate, under conventional condensation conditions.

As a rule, the condensation is carried out at from 20° to 120° C.

The cyclization to give the pyran derivative may be carried out together with the condensation, or subsequent thereto, in the same process step or in a separate process step. The cyclization is carried out in the conventional manner in the presence of a base, such as sodium hydroxide, potassium hydroxide, sodium carbonate, potassium carbonate, sodium acetate, potassium acetate, ammonia, an aliphatic amine or pyridine. The crystalline spirodipyran compound which separates out from this solution can be used—either directly or after purification, e.g., by recrystallization or reprecipitation—as a dye-forming component for copying processes.

Examples of suitable starting compounds of the formulae II, III and V for the manufacture of the compounds (IV) are:

(a) Pyrylium salts of the formula II in the form of their chlorides, perchlorates, tetrafluoborates, tetrachloroferrates and trichlorozincates: A 2,3-dimethyl-benzopyrylium salt, 2-methyl-3-i-propyl-benzopyrylium salt, 2-methyl-3-i-butyl-benzopyrylium salt, 2,3-tetramethylenebenzopyrylium salt, 2-methyl-3-decyl-benzopyrylium salt, 2-methyl-3-i-benzopyrylium salt, 2-methyl-3-n-pentylbenzopyrylium salt, 2,3-dimethyl-6-chloro-benzopyrylium salt, 2-methyl-3-ethyl-benzopyrylium salt, 2,3-dimethyl-6-bromo-benzopyrylium salt, 2-methyl-3-phenyl-benzopyrylium salt, 2-methyl-3-benzyl-benzopyrylium salt, 2,3-dimethyl-8-methoxy-benzopyrylium salt, 2,3-dimethyl-7-methoxy-benzopyrylium salt, 2,3-(γ-tert.-butyl-tetramethylene)-benzopyrylium salt, 2,3-dimethyl-8-carbomethoxy-benzopyrylium salt, 2,3-dimethyl-8-carboethoxy-benzopyrylium salt, 2,3-dimethyl-6-tert.-butyl-benzopyrylium salt, 2,3-dimethyl-6-nitro-benzopyrylium salt, 2,3,6-trimethyl-benzopyrylium salt, 2-methyl-3-nonyl-benzopyrylium salt, 2-methyl-3-phenethyl-benzopyrylium salt, 2-methyl-3-(4'-methylphenyl)-benzopyrylium salt, 2-methyl-3-(4'-chlorophenyl)-benzopyrylium salt, 2,3-(γ-octyl-tetramethylene)-benzopyrylium salt, 2,3-(γ-dodecyl-tetramethylene)-benzopyrylium salt, 2,3-(γ-nonyl-tetramethylene)-benzopyrylium salt, 2,3-(β,γ,γ-trimethyl-tetramethylene)-benzopyrylium salt, 2,3-dimethyl-naphtho(2,1-b)pyrylium salt, 2,3-dimethyl-7-chloro-naphtho(2,1-b)pyrylium salt, 2,3-dimethyl-7-bromonaphtho(2,1-b)pyrylium salt, 2,3-dimethyl-10-carbomethoxy-naphtho(2,1-b)pyrylium salt, 2,3-tetramethylene-naphtho(2,1-b)pyrylium salt, 2,3-(γ-tert.-butyl-tetramethylene)-naphtho(2,1-b)pyrylium salt, 2-methyl-3-i-propyl-naphtho (2,1-b)pyrylium salt, 2-methyl-3-i-butyl-naphtho(2,1-b) pyrylium salt, 2-methyl-3-i-pentyl-naphtho(2,1-b)pyrylium salt and 2,3-dimethyl-10-carboethoxy-naphtho(2,1-b)pyrylium salt.

(b) Aldehydes of the formula III: 4-N-morpholinyl-salicylaldehyde, 4-N-isoindolinyl-salicylaldehyde, 4-N-(N'-methyl)-piperazinyl-salicylaldehyde, 4-N-(3',5'-dimethyl)-morpholinyl-salicylaldehyde and 4-(N-thiomorpholinesulfonyl)-salicylaldehyde.

(c) Chalcones of the formula V: 1-o-hydroxyphenyl-2-phenyl-but-1-en-3-one, 1-o-hydroxyphenyl-2-p-tolyl-but-1-en-3-one and 1-o-hydroxyphenyl-2-p-chlorophenyl-but-1-en-3-one.

The Examples which follow further illustrate the manufacture and isolation of the compounds of the formula I. In the Examples, parts are by weight.

EXAMPLE 1

165 parts of 2,3-dimethyl-benzopyrylium trichlorozincate and 105 parts of 4-N-morpholinylsalicylaldehyde in 900 parts of methanol are refluxed for two hours. The crystalline dye is isolated from the cooled reaction mixture and is stirred in 500 parts of 25% strength ammonia solution and 1,000 parts of toluene until the color has lightened completely. The toluene phase is separated off, dried with sodium sulfate and concentrated to one-third of its original volume. On adding 250 parts of methanol to this solution, 130 parts of 3'-methyl-7-N-morpholinyl-2,2'-spirodi-(2H-1-benzopyran) of the formula

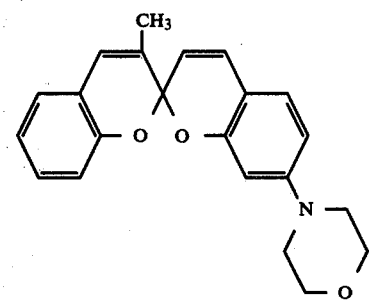

precipitate. Melting point 136°–138° C.

A solution of this compound is micro-encapsulated and the capsules are coated onto paper. The paper is placed on an acid receptive coating and on writing on the paper, the capsules are destroyed and their contents are brought into contact with the receptive coating, resulting in an intense blue copy.

Because of the very limited capacity of the dye-forming component to develop a color without an acceptor, virtually no color (mirror image) is produced on the sheet carrying the capsule layer by the dye-forming component solution released from the destroyed capsules.

The dye-forming component also exhibits this low tendency to produce a coloration when a copy is made on uncoated paper, where virtually no color results, whilst a dye-forming component containing a diethylamino group instead of the morpholine ring produces a clearly visible, blue copy.

EXAMPLES 2 TO 33

Dye-forming components of the formula

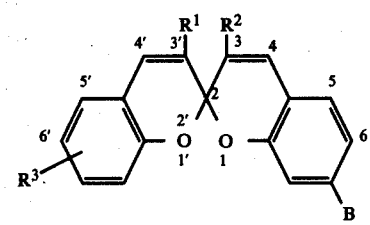

are prepared by methods similar to that described in Example 1.

| No. | $R^1$ | $R^2$ | $R^3$ | —B | Hue |
|---|---|---|---|---|---|
| 2 | CH(CH$_3$)$_2$ | H | — | —N◯O | blue |

-continued

| No. | R¹ | R² | R³ | —B | Hue |
|---|---|---|---|---|---|
| 3 | CH₃ | H | — | 2,6-dimethylmorpholino | blue |
| 4 | CH₃ | H | 6'-Cl | morpholino | blue |
| 5 | CH₃ | H | 6'-Br | morpholino | blue |
| 6 | CH₃ | H | 8'-CO₂CH₃ | morpholino | blue |
| 7 | CH₃ | H | — | 4-methylpiperazino | blue |
| 8 | —(CH₂)₃— | | — | morpholino | violet blue |
| 9 | —CH₂—CH(C₄H₉-(tert.))—CH₂— | | — | morpholino | violet blue |
| 10 | —CH₂—CH(C₈H₁₇(n))—CH₂— | | — | morpholino | violet blue |
| 11 | —CH₂—CH(C₁₂H₂₅(n))—CH₂— | | — | morpholino | violet blue |
| 12 | CH₃ | H | 8'-CO₂C₂H₅ | morpholino | blue |
| 13 | CH₃ | H | 6'-C₄H₉-(tert) | morpholino | blue |
| 14 | CH₃ | H | 6'-NO₂ | morpholino | violet blue |
| 15 | CH₃ | H | 6'-CH₃ | morpholino | blue |
| 16 | CH₃ | H | 8'-OCH₃ | morpholino | blue |
| 17 | C₁₆H₃₃ | H | — | morpholino | blue |
| 18 | p-H₃CC₆H₄ | H | — | morpholino | blue |
| 19 | p-ClC₆H₄ | H | — | morpholino | blue |
| 20 | C₅H₁₁(n) | H | — | morpholino | blue |
| 21 | C₂H₄C₆H₅ | H | — | morpholino | blue |

-continued

| No. | R¹ | R² | R³ | —B | Hue |
|---|---|---|---|---|---|
| 22 | CH₂C₆H₅ | H | — | —N(morpholine) | blue |
| 23 | —CH(CH₃)—CH₂—CH(CH₃)—CH₃ | | — | —N(morpholine) | reddish violet |
| 24 | —CH₂—CH(C₉H₁₉(n))—CH₂— | | — | —N(morpholine) | violet blue |
| 25 | C₆H₅ | H | — | —N(morpholine) | blue |
| 26 | C₅H₁₁(n) | H | — | —N(morpholine) | blue |
| 27 | C₁₀H₁₁(n) | H | — | —N(morpholine) | blue |
| 28 | C₁₆H₃₃ | H | — | —N(morpholine) | blue |
| 29 | CH₃ | H | 6'-CH₃ | —N(morpholine) | blue |
| 30 | —CH₂—CH(C₉H₁₉(n))—CH₂— | | — | —N(morpholine) | violet blue |
| 31 | CH₃ | H | — | —N(isoindoline) | blue |
| 32 | i-C₃H₇ | H | — | —N(isoindoline) | blue |
| 33 | CH₃ | H | — | —N(thiomorpholine-SO₂) | violet blue |
| 34 | —C₂H₅ | H | — | —N(morpholine) | blue |

EXAMPLE 35

19 parts of 2,3-dimethyl-naphthopyrylium trichlorozincate and 11 parts of 4-N-morpholinylsalicylaldehyde in 150 parts of alcohol are refluxed for two hours. The crystalline dye is isolated and converted to the colorless spirodipyran formed by the method described in Example 1. 13 parts of the dye-forming component 3'-methyl-7-N-morpholinyl-spiro-(2H-1-benzopyran)-2,2'-(2H)-naphtho(2,1-b)-pyran of the formula

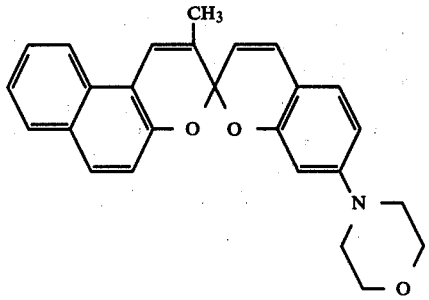

are obtained, melting at 154°–155° C.

In contact with acidic materials, the compound develops a blue coloration.

In contrast, virtually no color is developed on paper which has not been coated with an electron acceptor. On the other hand, a comparatively intense bluish green color is developed by a dye-forming component in which the 7-position is substituted by a diethylamino group instead of the morpholine ring.

EXAMPLE 36

Following the method described in Example 35, 21 parts of 2-methyl-3-i-butyl-naphthopyrylium trichlorozincate and 11 parts of 4-N-morpholinylsalicylaldehyde in 300 parts of alcohol are refluxed for two hours.

5 parts of 3'-i-butyl-7-N-morpholinyl-spiro-(2H-1-benzopyran)-2,2'-(2H)-naphtho(2,1-b)pyran of the formula

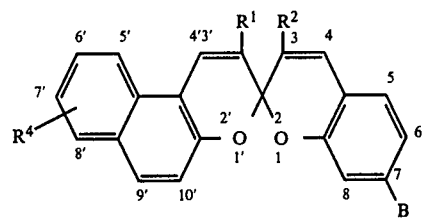

are obtained. The dye-forming component melts at 101°–102° C. and gives a blue coloration with electron acceptors.

EXAMPLES 37 TO 45

The dye-forming components of the formula

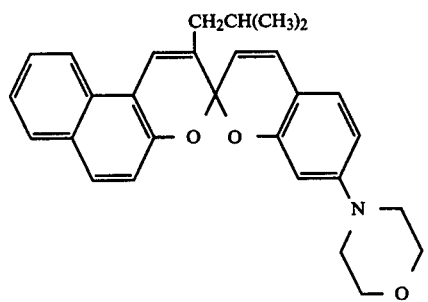

are obtained by the method described in Examples 35 and 36.

The Table which follows gives the meanings of the substituents $R^1$, $R^2$, $R^4$ and -B and the hues developed on contact with acidic materials.

| No. | $R^1$ | $R^2$ | $R^4$ | —B | Hue |
|---|---|---|---|---|---|
| 37 | i-$C_5H_{11}$ | H | — | —N(morpholino) | blue |
| 38 | i-$C_3H_7$ | H | — | —N(morpholino) | blue |
| 39 | $CH_3$ | H | 7'-Cl | —N(morpholino) | blue |
| 40 | $CH_3$ | H | 7'-Br | —N(morpholino) | blue |
| 41 | $CH_3$ | H | 10'-$CO_2CH_3$ | —N(morpholino) | blue |
| 42 | $CH_3$ | H | 10'-$CO_2C_2H_5$ | —N(morpholino) | blue |
| 43 | —$(CH_2)_3$— | | — | —N(morpholino) | blue |
| 44 | —$CH_2$—CH—$CH_2$— (with $C_4H_9$(tert.)) | | — | —N(morpholino) | blue |
| 45 | $CH_3$ | H | — | —N(isoindoline) | blue |

We claim:
1. A spirodipyran of the general formula

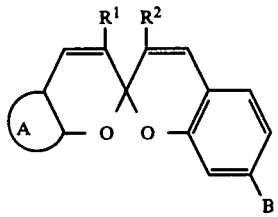

where
A is the radical of a fused benzene ring which is unsubstituted or is substituted by alkyl of 1 to 4 carbon atoms, alkoxy of 1 to 4 carbon atoms, nitro, chlorine, bromine or carboalkoxy (where alkoxy is of 1 to 6 carbon atoms), or is the radical of a naphthalene ring fused in the 2,1-position, which is unsubstituted or substituted by chlorine, bromine or carboalkoxy (where alkoxy is of 1 to 6 carbon atoms), $R^1$ is alkyl of 1 to 16 carbon atoms or is phenyl which is unsubstituted or substituted by alkyl of 1 to 4 carbon atoms, alkoxy of 1 to 4 carbon atoms, chlorine or bromine, or is phenalkyl of 7 to 10 carbon atoms and $R^2$ is hydrogen, or $R^1$ and $R^2$ together are a trimethylene bridge which is unsubstituted or in which one, two or three H atoms are replaced by alkyl of 1 to 12 carbon atoms, and B is N-morpholinyl, which is unsubstituted or substituted by one or two methyl, or is N-thiomorpholinyl-S-dioxide, N-(N'-alkyl)-piperazinyl (where alkyl is of 1 to 4 carbon atoms) or N-isoindolinyl.

2. A spirodipyran as claimed in claim 1, wherein B is N-morpholinyl.

3. A spirodipyran as claimed in claim 1, where
$R^1$ is alkyl of 1 to 4 carbon atoms, methoxyphenyl, ethoxyphenyl, ethylphenyl, methylphenyl or chlorophenyl,
$R^2$ is hydrogen and
B is N-morpholinyl and
A has the meaning given in claim 1.

4. A spirodipyran as claimed in claim 3, wherein
A is a fused benzene ring which is unsubstituted or substituted by methyl, ethyl, methoxy, ethoxy or carboalkoxy, where alkoxy is of 1 to 4 carbon atoms, or is a fused 2,1-naphthalene ring which is substituted or substituted by carboalkoxy, where alkoxy is of 1 to 4 carbon atoms.

5. A spirodipyran as claimed in claim 1, where
$R^1$ is alkyl of 1 to 4 carbon atoms,
$R^2$ is hydrogen and
B is N-morpholinyl and
A has the meaning given in claim 1.

6. A spirodipyran as claimed in claim 1, where
$R^1$ is alkyl of 1 to 4 carbon atoms,
$R^2$ is hydrogen,
A is the fused unsubstituted radical of a benzene or 2,1-naphthalene ring and
B is N-morpholinyl.

7. A spirodipyran as claimed in claim 1, where
$R^2$ is hydrogen,
$R^1$ is methyl, ethyl, isopropyl or isobutyl,
A is the radical of an unsubstituted fused benzene or 2,1-naphthalene ring and
B is N-morpholinyl.

* * * * *